(12) United States Patent
Altieri et al.

(10) Patent No.: US 7,794,926 B2
(45) Date of Patent: *Sep. 14, 2010

(54) DETECTION OF SURVIVIN IN THE BIOLOGICAL FLUIDS OF CANCER PATIENTS

(75) Inventors: Dario Altieri, Worcester, MA (US); Robert Weiss, North Haven, CT (US); Shannon Smith, Guilford, CT (US); Victor Morris, legal representative, Guilford, CT (US); Marcia Wheeler, Branford, CT (US); Janet Plescia, Meriden, CT (US)

(73) Assignee: Yale University, New Haven, CT (US)

( * ) Notice: Subject to any disclaimer, the term of this patent is extended or adjusted under 35 U.S.C. 154(b) by 0 days.

This patent is subject to a terminal disclaimer.

(21) Appl. No.: 11/405,694

(22) Filed: Apr. 18, 2006

(65) Prior Publication Data

US 2007/0065842 A1    Mar. 22, 2007

Related U.S. Application Data

(63) Continuation of application No. 10/042,302, filed on Jan. 11, 2002, now Pat. No. 7,097,966.

(60) Provisional application No. 60/260,898, filed on Jan. 12, 2001.

(51) Int. Cl.
| | |
|---|---|
| C12Q 1/00 | (2006.01) |
| C12Q 1/68 | (2006.01) |
| G01N 33/53 | (2006.01) |
| G01N 33/567 | (2006.01) |
| G01N 33/574 | (2006.01) |
| C12P 13/34 | (2006.01) |
| C12N 9/00 | (2006.01) |
| C07H 1/00 | (2006.01) |
| C07K 21/04 | (2006.01) |

(52) U.S. Cl. ............... 435/4; 435/6; 435/7.1; 435/7.21; 435/7.23; 435/91.1; 435/183; 436/63; 436/64; 436/86; 436/164; 530/350; 530/385; 530/386; 530/387.1; 530/388.1; 530/388.15; 530/389.1; 536/24.31; 536/24.33

(58) Field of Classification Search ............ 435/4, 435/6, 7.1, 7.21, 7.23, 91.1, 183; 436/63, 436/64, 86, 164; 530/350, 385, 386, 387.1, 530/388.1, 388.15, 389.1; 536/24.31, 24.33
See application file for complete search history.

(56) References Cited

U.S. PATENT DOCUMENTS

| | | | | |
|---|---|---|---|---|
| 5,998,216 | A * | 12/1999 | O'Donnell | 436/176 |
| 6,184,030 | B1 * | 2/2001 | Katoot et al. | 435/287.2 |
| 6,656,684 | B1 * | 12/2003 | Sandler | 435/6 |
| 6,673,914 | B1 | 1/2004 | Hoon | |
| 7,097,966 | B2 | 8/2006 | Altieri et al. | |

FOREIGN PATENT DOCUMENTS

| | | |
|---|---|---|
| WO | WO 98/22589 | 5/1998 |
| WO | WO 01/53535 | 7/2001 |

OTHER PUBLICATIONS

Bio-Rad Laboratories Catalog 1998/99.*
Jouben-Steele et al. (Laboratory Investigation 1(79): 99A, Jan. 1999/ IDS reference submitted Nov. 18, 2002).*
Adida et al. "Expression and prognostic significance of survivin in de novo acute myeloid leukaemia" Br. J. Haematol., 2000, 111(1):196-203.
Adida et al., "Anti-apoptosis gene, survivin, and prognosis of neuroblastoma" Lancet, 1998, 351: 882-883.
Alexandroff et al., "BCG immunotherapy of bladder cancer: 20 years on" Lancet, 1999, 353:1689.
Ambrosini et al., "A novel anti-apoptosis gene, survivin, expressed in cancer and lymphoma" Nat. Med., 1997, 3: 917-921.
Bio-Rad Laboratories. Bio-Rad Catolog 1998/1999, pp. 246 and 247.
Deveraux et al., "IAP family proteins—suppressors of apoptosis" Genes Dev., 1999, 13: 239-252.
Gazzaniga et al., "Bcl-2/bax mRNA expression ratio as prognostic factor in low-grade urinary bladder cancer" Int. J. Cancer, 1996, 69:100-104.
Grossman et al., "Expression and targeting of the apoptosis inhibitor, survivin, in human melanoma" J. Invest. Dermatol., 1999, 113: 1076-1081.
Islam et al., "High expression of Survivin, mapped to 17q25, is significantly associated with poor prognostic factors and promotes cell survival in human neuroblastoma" Oncogene, 2000,19: 617-623.
Jouben-Steele et al., Laboratory Investigation, United States and Canadian Academy of Pathology, vol. 1, No. 79, Jan. 1999, pp. 99A, AN569, abstract.
Kawasaki et al., "Inhibition of apoptosis by survivin predicts shorter survival rates in colorectal cancer" Cancer Res., 1998, 58: 5071-5074.
Lara et al., "Apoptosis in carcinoma of the bladder: relation with radiation treatment results" Int. J. Radiat. Oncol. Biol. Phys., 1999, 43:1015-1019.
Lu et al., "Expression of a novel antiapoptosis gene, survivin, correlated with tumor cell apoptosis and p53 accumulation in gastric carcinomas" Cancer Res., 1998, 58: 1808-1812.
Monzo et al., "A novel anti-apoptosis gene: Re-expression of survivin messenger RNA as a prognosis marker in non-small-cell lung cancers" J. Clin. Oncol., 1999, 17: 2100-2104.

(Continued)

*Primary Examiner*—Alana M Harris
(74) *Attorney, Agent, or Firm*—Morgan, Lewis & Bockius LLP (57) ABSTRACT

The present invention includes a method for diagnosing cancer comprising detecting the presence of survivin in the biological fluid of a patient. The present invention also provides kits comprising one or more agents that detect survivin polypeptide or survivin nucleic acid and a container for collecting biological fluid for testing.

47 Claims, 4 Drawing Sheets

OTHER PUBLICATIONS

Moore, "Urine detection of survivin and diagnosis of bladder cancer" Journal of Insurance Medicine, vol. 33, No. 2, May 8, 2001, pp. 202-203.

Ozen, "Bladder cancer" Curr. Opin. Oncol., 1998, 10: 273-278.

Reed, "Dysregulation of apoptosis in cancer" J. Clin. Oncol., 1999, 17: 2941-2953.

Roy et al., "The gene for neuronal apoptosis inhibitory protein is partially deleted in individuals with spinal muscular atrophy" Cell, 1995, 80:167-178.

Sarela et al., "Expression of the antiapoptosis gene, survivin, predicts death from recurrent colorectal carcinoma", Gut, vol. 46, No. 5, May 2000, pp. 645-650.

Smith et al., "Urine detection of survivin and diagnosis of bladder cancer" Journal of American Medical Association, 2001, 285:324-328.

Stein et al., "Prognostic markers in bladder cancer: a contemporary review of the literature" J. Urol., 1998, 160: 645-659.

Sternberg et al., "Methotrexate, vinblastine, doxorubicin, and cisplatin for advanced transitional cell carcinoma of the urothelium. Efficacy and patterns of response and relapse" Cancer, 1989, 64: 2448-2458.

Swana et al., "Tumor content of the antiapoptosis molecule survivin and recurrence of bladder cancer" N. Engl. J. Med., 1999, 341:452-453.

Tanaka et al., "Expression of survivin and its relationship to loss of apoptosis in breast carcinomas" Clin. Cancer Res., 2000, 6: 127-134.

Velculescu et al., "Analysis of human transcriptomes" Nat. Genet., 1999, 23:387-388.

Von der Masse, 2002, Seminars in Oncology, 29(1, Suppl. 3): 3-14.

Williams and Wilkins, Illustrated Stedman's Medicinal Dictionary, 24th edition, p. 542, 1269, and 1370, Baltimore, MD, 1982.

* cited by examiner

FIG.1

| 0 | RCC | TCC | TCC/R | TCC/R | Ctrl |
|---|---|---|---|---|---|
| 0.001 | PC | TCC | TCC/R | TCC/R | Ctrl |
| 0.005 | PC | TCC | TCC/R | TCC/R | Ctrl |
| 0.01 | PC | TCC | TCC/R | TCC/R | Ctrl |
| 0.05 | PC | TCC | TCC/R | TCC/R | Ctrl |
| 0.25 | PSA | TCC/R | TCC/T | TCC/R | Ctrl |
| 1 | BPH | TCC | TCC/R | TCC/R | Ctrl |

DETECTION OF SURVIVIN IN THE BIOLOGICAL FLUIDS OF CANCER PATIENTS

RELATED APPLICATION

This is a continuation application of U.S. application Ser. No. 10/042,302, filed Jan. 11, 2002 now U.S. Pat. No. 7,097,966, which claims the benefit of U.S. Provisional Application 60/260,898, filed Jan. 12, 2001, both of which are hereby incorporated by reference in their entirety.

ACKNOWLEDGMENT OF FEDERAL SUPPORT

This invention was made with government support under Grant CA 78810, DK02499, and DK38311 awarded by the NIH. The government has certain rights in the invention.

FIELD OF THE INVENTION

The present invention relates to a method of diagnosing cancer comprising detecting the presence of survivin in the biological fluids of a patient. Specifically, the method relates to the diagnosis of bladder cancer, comprising detecting the presence of survivin in urine samples of a patient. Additionally, the present invention relates to kits for diagnosing cancer comprising an agent that detects survivin in the biological fluids of a patient and a container for collecting the biological fluids.

BACKGROUND

Cancer refers to malignant neoplasms that tend to invade surrounding tissues and that metastasize to new body sites. They are likely to recur after attempted removal and to cause death of the patient unless adequately treated. The exact cause of cancer is not known, but links between certain activities such as smoking or exposure to carcinogens and the incidence of certain types of cancers and tumors have been shown by a number of researchers.

The spread of cancer from a primary site to distant organs, i.e., metastasis, still remains the main cause of death for most cancer patients. Despite years of research, the genetic mechanisms involved in the process remain largely uncharacterized. Such information is of special importance in cancer prognosis given the uncertain course of the disease. Since cancer prognosis cannot always be accurately assessed using current tumor grading techniques, one of the greatest obstacles to the successful treatment of the cancer patient continues to be the lack of sound prognostic markers.

Bladder Cancer

Bladder cancer is a malignant tumor growth which usually arises from the urothelial cells, (transitional cells) that line the bladder. Urothelial carcinoma of the bladder, i.e. bladder cancer, is the fourth most common cancer in men and the eighth most common cancer in women in the United States, accounting for more than 54,000 new cases and 11,200 deaths every year. Recurrences of bladder cancer occur in up to 80% of patients and constitute a formidable obstacle to long-lasting remissions, with such recurrences frequently involving muscle invasion and disseminated disease (Dawson et al., ABC of Urology: Urological Malignancies-II: Urothelial Tumors. BMJ, 1996, 312: 1090-94).

Numerous factors may contribute to the development of bladder cancer. Cigarette smoking and occupational exposure to a certain class of organic chemicals called aromatic amines (beta-naphthylamines, xenylamine, 4-nitrobiphenyl, benzidine) are well-established risk factors. Some studies indicate that there may be a link between high doses of the artificial sweetener saccharin and transitional cell bladder cancer. Other studies have shown that women who received radiation therapy for the treatment of cervical cancer have an increased risk of developing transitional cell bladder cancer. Additionally, people who received the chemotherapy drug, cyclophosphamide (Cytoxan), have demonstrated a greater risk of developing bladder cancer.

The most common clinical presentation of bladder cancer is hematuria. Frequently, however, the diagnosis of bladder cancer is delayed because the hematuria is either intermittent or attributed to other causes, such as a urinary tract infection or the use of anti-coagulants. Voided urine cytology of transitional cells is conventionally used to diagnose bladder cancer. If the urinary cytology is positive, then transitional cell cancer of the urothelium is almost certainly present. However, cytological examination of transitional cells may be negative in up to half of the patients with bladder cancer. Thus, negative cytological results do not rule out the presence of bladder cancer (Badalament et al., Cancer, 1987, 59(12): 2078; Cohen et al., Urologic Clinics of North America, 1992, 19(3): 421).

As an added diagnostic complication, the entire urinary tract must be evaluated for transitional cell cancer once an initial diagnosis of bladder cancer is made because transitional cells line the urinary tract starting at the level of the kidneys, including the renal pelvis, the ureters, the bladder, and most of the urethra. The renal pelvis of the kidneys and ureters is best evaluated by intravenous pyelogram (IVP) or retrograde pyelogram. An IVP involves an intravenous injection of contrast material which is then filtered out of the blood into the urine by the kidney. Plain x-rays taken during this process show the urinary tract. Typically a retrograde pyelogram is reserved for patients with an intravenous contrast allergy or poor visualization on IVP. A retrograde pyelogram is performed at the time of cystoscopy.

Cystoscopy, which involves the use of a lighted instrument to view inside the bladder, is an uncomfortable procedure utilized for the unambiguous diagnosis of bladder cancer. In performing a retrograde pyelogram through the cystoscope a small plastic tube is inserted into the ureter, and contrast material is injected into the ureter and kidney. Cystoscopy enables the identification of small subtle abnormalities that may be missed by other diagnostic modalities such as ultrasound, computed tomography, or magnetic resonance imaging. Thus, office cystoscopy is an essential part of the initial evaluation and at this time cannot be substituted by other tests. Today, most office cystoscopic examinations are performed with a flexible scope. Compared to rigid cystoscopy, flexible endoscopy is more comfortable and allows the physician to see around the curves of an enlarged prostate.

A biopsy may also be performed to diagnose bladder cancer. A biopsy is the removal of a small sample of living tissue from an organ, such as the bladder, for microscopic examination to confirm or establish a diagnosis, estimate prognosis, or follow the course of a disease. However, biopsies are invasive procedures, and are therefore not desirable and it frequently is necessary for a person to undergo anesthesia. In addition, as with any invasive procedure, an individual undergoing biopsy runs the risk of infection. Further, the entire bladder cannot be biopsied to determine whether bladder cancer is present.

Staging Bladder Cancer

Bladder cancers are classified based on their aggressiveness and how different they are from the surrounding bladder tissue (differentiation). They are staged and graded by physicians while diagnosing bladder cancer.

There are several different ways to stage tumors. The two most commonly used staging systems for bladder cancer are the ABCD system (the Jewett-Strong-Marshall system) and the TNM system. The ABCD system is older and uses A-B-C-D staging to classify the distinct phases or periods of bladder cancer. The system basically uses the following scale: 0, carcinoma in situ (tumor limited to the bladder mucosa (lining)); A, tumor extends through the mucosa but does not extend beyond the submucosa; B, tumor invades the muscle; C, tumor invades into the fat; and D, cancer has spread to regional lymph nodes or to distant sites. Each letter is followed by a number, for example A1, B2, etc. With the TNM system, the bladder is described by the T, the lymph nodes by the N, and distant spread by the M. Each letter is followed by a describing number, T2aN0M0. For example, Ta denotes a non-invasive papillary carcinoma; Tis denotes a carcinoma in situ; and T1 denotes a tumor invading subepithelial connective tissue.

Bladder cancers spread to the rest of the body by extending into the nearby organs, including the prostate, uterus, vagina, ureters, and rectum. Metastasis occurs through the pelvic lymph nodes, where the tumor next spreads to the liver, lungs and bones.

Grading Bladder Cancer

Bladder cancers are graded by a pathologist from the biopsy. The grade of a cancer provides information regarding how fast the cancer might be growing or how aggressive it might be. High grade cancers grow faster and spread earlier than low grade cancers. The current system of grading uses only three different grades: well-differentiated, moderately differentiated, and poorly differentiated (or Grade I, II or III). Some pathologists will use a 4-level grading system, I, II, III and IV. Either system is acceptable, and the pathologist will always note how many levels they use by declaring the cancer as a II/III or II/IV. The denominator or second number states what system they use. A well-differentiated tumor means that the cancer has more resemblance to normal bladder tissue and therefore usually does not grow or spread quickly. A poorly differentiated tumor means that the cancer does not resemble normal bladder and usually grows quickly and spreads to other tissues earlier. Moderately differentiated tumors are in the middle.

Grade, while important, has less bearing on the treatment decisions than does the stage. After the grade and stage are known, other factors also come into play before making any decision about future treatment.

Prostate Cancer

Prostate cancer is a malignant tumor growth within the prostate gland. It is the third most common cause of death from cancer among men of all ages and is the most common cause of death from cancer in men over 75 years old. Prostate cancer is rarely found in men younger than 40 years of age.

Although the cause is unknown, some studies have shown a relationship between prostate cancer and high dietary fat intake and increased testosterone levels. There is no known association with benign prostatic hyperplasia (BPH).

Like bladder cancer, prostate cancers are classified or staged based on their aggressiveness and the degree that they are different from the surrounding prostate tissue. Most prostate cancers are staged using the A-B-C-D staging system or the TNM system. For prostate cancer, the A-B-C-D system basically categorizes tumors using the following scale: A tumor not palpable (able to be felt) but detectable in microscopic biopsy; B palpable tumor confined to prostate; C extension of tumor beyond prostate with no distant metastasis; and D cancer has spread to regional lymph nodes. The TNM system, on the other hand, describes the prostate (T), the lymph nodes (N), and evidence of metastatic disease (distant spread) (M) separately. Prostate cancers spread by extending into the seminal vesicles, bladder, and peritoneal cavity. Prostate cancers typically metastasize to the lymph nodes, bones, lungs, liver, and kidneys.

Today, prostate cancer is usually graded using the Gleason grading system, named after a pathologist from the University of Minnesota. The system involves looking for different patterns of aggressiveness within the prostate and then giving two scores of 1-5. These two scores are added up to give the total Gleason score which will range from 2-10. The higher the score, the more aggressive the tumor will be. For example, a typical Gleason graded cancer might be written as Gleason 4+3=7, or Gleason 2+2=4.

Survivin

Deregulated expression of inhibitors of apoptosis (programmed cell death) is thought to contribute to cancer by abnormally extending cell viability, favoring the accumulation of mutations, and promoting resistance to therapy (Reed, J. Clin. Oncol., 1999, 17: 2941-53). A novel modulator of the cell death/viability balance in cancer was recently identified as survivin (Ambrosini et al., Nat. Med., 1997, 3: 917-21), a member of the Inhibitor of Apoptosis (IAP) gene family (Deveraux et al., Genes Dev., 1999, 13: 239-52).

Survivin is a 16.5 kDa cytoplasmic protein containing a single partially conserved BIR (baculovirus IAP repeats) domain, and a highly charged carboxyl-terminal coiled-coil region instead of a RING finger, which inhibits apoptosis induced by growth factor (IL-3) withdrawal when transferred in B cell precursors (Ambrosini et al., Nat Med 1997, 3:917-921). Based on overall sequence conservation, the absence of a carboxyl-terminal RING finger and the presence of a single, partially conserved BIR domain, survivin is the most distantly related member of the IAP family, sharing the highest degree of similarity with NAIP (neuronal apoptosis inhibitory protein; Roy et al., Cell, 1995, 80:167-178). Additionally, unlike other IAP proteins, survivin is undetectable in normal adult tissues, but becomes the top fourth transcript expressed in common human cancers (Ambrosini et al., Nat. Med., 1997, 3: 917-21; Velculescu et al., Nat. Genet., 1999, 23:387-88), such as lung, colon, breast, pancreas, and prostate, and in ~50% of high-grade non-Hodgkin's lymphomas, in vivo. Consistent with a proposed role of deregulated apoptosis in urothelial cancer (Gazzaniga et al., Int. J. Cancer, 1996, 69:100-04; Lara et al., Int. J. Radiat. Oncol. Biol. Phys., 1999, 43:1015-19), survivin was found in 78% of bladder cancers, but not in normal urothelium, and its expression correlated with accelerated recurrences (Swana et al., N. Engl. J. Med., 1999, 341:452-53). Because of its over-expression in cancer but not in normal tissues (Ambrosini et al., Nat. Med., 1997, 3:917-21; Velculescu et al., Nat. Genet., 1999, 23: 387-88), and its unfavorable predictive/prognostic significance in various malignancies (Adida et al., Lancet, 1998, 351: 882-83; Islam et al., Oncogene, 2000, 19: 617-23; Tanaka et al., Clin. Cancer Res., 2000, 6: 127-34; Monzo et al., J. Clin. Oncol., 1999, 17: 2100-04; Kawasaki et al., Cancer Res., 1998, 58: 5071-74), survivin may constitute a useful molecular marker in cancer. This is particularly relevant in bladder cancer (Stein et al., J. Urol., 1998, 160: 645-59; Ozen, Curr. Opin. Oncol., 1998, 10: 273-78) where simple and non-invasive diagnostic means to monitor response to therapy and simplify follow up protocols are urgently needed. Although regarded as "gold standard" (Brown, Urol. Clin. North Am., 2000, 27: 25-37), urine cytology has a low sensitivity (30-40%) in bladder cancer, and fails to detect superficial, low-grade lesions.

Accordingly, the inventors of the instant application investigated the potential suitability of bodily fluid survivin as a new molecular marker for detection of cancer, specifically detection of urine survivin for the diagnosis of bladder cancer.

SUMMARY OF THE INVENTION

The present invention provides a method of diagnosing cancer in a patient comprising assaying a sample of biological fluid from a patient for the presence or absence of survivin, wherein the presence of survivin in the sample indicates that the patient has cancer. In a preferred embodiment, the biological fluid is selected from the group consisting of prostatic fluid, seminal fluid, whole blood, serum, urine, breast biopsy fluid, gastrointestinal fluid, and vaginal fluid, and the cancer is new onset or recurrent cancer selected from the group consisting of lung cancer, colon cancer, breast cancer, pancreatic cancer, prostate cancer, bladder cancer, renal cancer, genitourinary tract cancer, non-hodgkin's lymphoma, and neuroblastoma. More preferably, the biological fluid is urine or blood serum, and the cancer is bladder or prostate cancer. Most preferably, the biological fluid is urine, and the cancer is bladder cancer.

In one aspect, the present invention contemplates a method to determine the grade of the cancer by quantitating the amount of survivin in the biological fluid of a patient, wherein a high level of survivin indicates that the cancer is of a high grade. Additionally, the present invention contemplates the use of the method to determine the stage of the cancer, wherein a cancer of the CIS stage has a higher level of survivin than the cancer of the non-invasive papillary carcinoma stage.

In another aspect, the present invention contemplates a method of monitoring cancer in a patient comprising quantitating the amount of survivin in the biological fluid of a patient. Additionally, the present invention contemplates determining the prognosis of a patient by detecting or quantitating the amount of survivin in the biological fluid of the patient. In some instances, the presence of survivin indicates a poor prognosis. Quantitation of survivin includes measuring relative levels of survivin in a sample. It may also include detection of the presence or absence of survivin.

Preferably, the survivin is detected using an agent that binds to survivin or hybridizes to the nucleic acid encoding survivin. Most preferably, the agent is selected from the group consisting of antibodies that bind survivin, survivin binding fragments, and nucleic acids that hybridize to a nucleic acid encoding survivin, and the agent is tagged with a label. The label may be a radioactive label, a fluorescent label, an enzyme, a chemiluminescent tag, or a colorimetric tag.

In one aspect of the invention, survivin is detected by an immunoassay. Preferably, the immunoassay is an enzyme linked immunosorbent assay or radioimmunoassay, and the immunoassay comprises immunoblotting, immunodiffusion, immunoelectrophoresis, or immunoprecipitation. More preferably, survivin is detected by dot blotting, most preferably, by using the Bio-Dot method and the Bio-Dot SF module.

In another aspect of the invention, survivin is detected by nucleic acid hybridization.

In a preferred embodiment, the nucleic acid hybridization is RT-PCR or Northern blot analysis. The agent used in nucleic acid hybridization is labeled with a radioactive label, a fluorescent label, an enzyme, a chemiluminescent tag, or a calorimetric tag.

The present invention also provides kits for diagnosis, prognosis, or monitoring cancer in a patient, comprising a container for collecting biological fluid from a patient and one or more agents that detect the presence of survivin in the biological fluid. The agents in the kit can be tagged with a label. Alternatively, other components can be included in the kit for tagging the agents. The present invention also contemplates kits comprising other components for diagnosing and monitoring cancer in a patient, and determining the prognosis of the cancer. In one embodiment, the components of the kit are packaged either in aqueous medium or in a lyophilized form.

BRIEF DESCRIPTION OF THE DRAWINGS

FIG. 4 shows serum detection of survivin using the Bio-Dot SF module. Increasing concentrations of recombinant survivin in μg/ml (left and right column), urine or serum samples were applied to a slot-blot apparatus. The membrane was incubated with an antibody to survivin followed by HRP-conjugated goat anti rabbit IgG. Bands were visualized by chemiluminescence. A number followed by "serum Bl CA" indicates serum from patients with TCC. Most of these samples were applied to the blot in duplicate. 7/8 serum samples from patients with bladder cancer were positive. One sample (8-serum Bl CA) was negative for one of the two samples tested. Urine and serum from patient 2 Bl CA were positive. "Urine Hx TCC" indicates urine from a single patient previously diagnosed with TCC. This patient was resected and is undergoing BCG treatment. "3-serum P CA" indicates survivin positive serum from a patient with prostate cancer. "6-serum BPH" is serum from a patient with benign prostate hypertrophy. This sample was survivin positive ½ times that it was tested. No addition information is available for this patient. "Urine TCC" is urine from a patient with bladder cancer. "Neg con" is a protein control. "Blank" is TBS buffer only.

DETAILED DESCRIPTION OF THE INVENTION

I. General Description

The present invention is based on the need to develop safe, reliable, non-invasive screening strategies for detecting cancer, specifically bladder cancer. The identification of a single predictive/prognostic marker of the disease has remained elusive (Stein et al., J. Urol. 1998, 160: 645-59). The identification of a marker and the development of a method to diagnose and screen for cancer, especially transitional cell carcinoma of the bladder, as well as for monitoring cancer activity and determining the prognosis of an individual having bladder cancer would be useful to the treatment of cancer.

The present invention discloses a simple, antibody or other probe based test to identify the apoptosis inhibitor, survivin, in the urine or other bodily fluid of patients with cancer.

The present invention is based in part on the discovery that urine survivin is found in all patients with newly diagnosed or recurrent bladder cancer (46/46), but not in normal volunteers (0/17), or in patients with other urologic cancers (0/30), and only in 4/30 patients with non-neoplastic genito-urinary disorders. The present invention is also based on the finding that of the three patients with hematuria who tested positive for urine survivin, one had a positive cytology for bladder cancer and another one was diagnosed with bladder cancer within six months of survivin detection. Moreover, the present invention is based on the finding that patients treated for bladder cancer and achieving cystoscopic remission are negative for urine survivin (32/35).

The present invention is also based in part on the finding that survivin is detected in the blood serum of patients with bladder and prostate cancer.

II. Specific Embodiments

1. Biological Fluids

As used herein, the term "biological fluids of patients" refers to fluids from living organisms. The term encompasses "bodily fluids" which are found in the body of living organisms.

The present invention includes the use of agents in the screening of biological fluids for the presence of survivin. In vitro serological evaluation of biological fluids withdrawn from patients thereby permits non-invasive diagnosis of cancers. For example, human bodily fluids such as prostatic fluid, seminal fluid, whole blood, serum, urine, breast biopsy fluid, gastrointestinal fluid, and vaginal fluid can be taken from a patient and assayed for the presence of survivin using an agent that can detect survivin by radioimmunoassays or enzyme-linked immunoassays, competitive binding enzyme-linked immunoassays, dot blot, Western blot, Northern blot, PCR, or other assays known in the art.

In a preferred embodiment, blood serum from patients is collected to detect the presence of survivin for diagnosis of bladder or prostate cancer.

More preferably, urine samples from patients are collected to detect the presence of survivin for diagnosis of bladder cancer. Urine samples to be tested may be collected well in advance of testing and frozen prior to treatment. If the urine sample is to be frozen prior to analysis, it is preferred that the sample be collected and placed on ice. Preferably within a time period of about 2 hours, the iced sample is centrifuged to pellet cellular debris, then filtered, and the filtrate then promptly frozen at −20° C., more preferably at −80° C. Just prior to analysis, frozen samples should be rapidly thawed in a 37° C. water bath. Fresh urine samples may also be used immediately after collection, optimal centrifugation, and filtration. More preferably, whole urine is kept on ice until it is frozen at −80° C. After thawing at 4° C., the urine is centrifuged at 4° C. and assayed for survivin.

2. Agents that Detect Survivin

Agents that are capable of detecting survivin in the biological fluids of patients are those that interact with survivin or the nucleic acid encoding survivin. Examples of such agents include, but are not limited to survivin antibodies or fragments thereof that bind survivin, survivin binding partners such as $p34^{cdc2}$-cyclin B1 kinase, and nucleic acids that hybridize to the nucleic acid encoding survivin.

Survivin Antibodies

Survivin antibodies have been prepared and used by the skilled artisan. Lu et al. (Cancer Res., 1998, 58(9): 1808-12) teach the preparation of mouse monoclonal survivin antibodies from recombinantly produced survivin/glutathione S-transferase fusion protein for immunohistochemical analysis of gastric carcinomas. Grossman et al. (J. Invest. Dermatol., 1999, 113: 1076-81) disclose the use of rabbit polyclonal antibodies to detect survivin in human metastatic malignant melanoma cell lines.

Survivin or survivin peptides may be used to raise antibodies using standard immunological procedures well known and described in the art (Practical Immunology, Butt, ed., Marchel Dekker, New York, 1984). Briefly, an isolated survivin or survivin peptide produced, for example, by recombinant DNA expression in a host cell, is used to raise antibodies in a xenogenic host. Preferred antibodies are antibodies that bind specifically to an epitope on the survivin protein, preferably having a binding affinity greater than about $10^5$ $M^{-1}$, most preferably having an affinity greater than about $10^7$ $M^{-1}$ for that epitope. For example, where antibodies to a human survivin protein are desired, a suitable antibody generating host is a mouse, goat, rabbit, guinea pig, or other mammal useful for generating antibodies. The survivin protein or peptide is combined with a suitable adjuvant capable of enhancing antibody production in the host, and injected into the host, for example, by intraperitoneal administration. Any adjuvant suitable for stimulating the host's immune response may be used. A currently preferred adjuvant is Freund's complete adjuvant (an emulsion comprising killed and dried microbial cells, e.g., from Calbiochem Corp., San Diego, or Gibco, Grand Island, N.Y.). Where multiple antigen injections are desired, the subsequent injections comprise the antigen in combination with an incomplete adjuvant (e.g. cell-free emulsion).

In a preferred embodiment, the disclosed method of detecting the presence of survivin in biological fluids is performed using antibodies that bind specifically to survivin. Polyclonal and monoclonal antibodies that bind specifically to survivin may be prepared by methods known in the art. Antibodies include recombinant polyclonal or monoclonal Fab fragments prepared in accordance with the method of Huse et al. (Science, 1989, 246: 1275-1281; see also Campbell, "Monoclonal Antibody Technology, The Production and Characterization of Rodent and Human Hybridomas" in Burdon et al., Eds, Laboratory Techniques in Biochemistry and Molecular Biology, 1985 Volume 13, Elsevier Science Publishers, Amsterdam).

As mentioned above, methods for preparing polyclonal and monoclonal antibodies are well known to the skilled artisan. Briefly, polyclonal antibodies may be produced by injecting a host mammal, such as a rabbit, mouse, rat, or goat, with the survivin protein or a survivin peptide or fragment. Sera from the mammal are extracted and screened to obtain polyclonal antibodies that are specific to the peptide or peptide fragment.

The survivin protein, peptide, or fragment for generation of antibodies may be obtained by isolation from its natural source, by recombinant means, or by synthetic means.

In order to produce monoclonal antibodies, a host mammal is inoculated with a survivin protein or peptide and then boosted. Spleens are collected from inoculated mammals a few days after the final boost. Cell suspensions from the spleens are fused with a tumor cell in accordance with the general method described by Kohler and Milstein (Nature, 1975, 256: 495-497). In order to be useful, a peptide fragment must contain sufficient amino acid residues to define the epitope of the survivin molecule being detected.

If the fragment is too short to be immunogenic, it may be conjugated to a carrier molecule. Some suitable carrier molecules include keyhole limpet hemocyanin and bovine serum albumin. Conjugation may be carried out by methods known in the art. One such method is to combine a cysteine residue of the fragment with a cysteine residue on the carrier molecule. The peptide fragments may be synthesized by methods known in the art. Some suitable methods are described by Stuart and Young in "Solid Phase Peptide Synthesis," Second Edition, Pierce Chemical Company (1984).

Purification of the antibodies or fragments can be accomplished by a variety of methods known to those of skill including, precipitation by ammonium sulfate or sodium sulfate followed by dialysis against saline, ion exchange chromatography, affinity or immunoaffinity chromatography as well as gel filtration, zone electrophoresis, etc. (Goding in, Monoclonal Antibodies: Principles and Practice, 2d ed., pp. 104-126, Orlando, Fla., Academic Press). It is preferable to use purified antibodies or purified fragments of the antibodies having at least a portion of a survivin binding region, including such as Fv, F(ab')$_2$, Fab fragments (Harlow and Lane, 1988, Antibody Cold Spring Harbor) for the detection of survivin in the fluids of cancer patients, preferably in the urine of bladder cancer patients.

For use in detection and/or monitoring of cancer, the purified antibodies can be covalently attached, either directly or via linker, to a compound which serves as a reporter group to permit detection of the presence of survivin. A variety of different types of substances can serve as the reporter group, including but not limited to enzymes, dyes, radioactive metal and non-metal isotopes, fluorogenic compounds, fluorescent compounds, etc. Methods for preparation of antibody conjugates of the antibodies (or fragments thereof) of the invention useful for detection, monitoring are described in U.S. Pat. Nos. 4,671,958; 4,741,900 and 4,867,973.

In one aspect of the invention, preferred binding epitopes may be identified from a known survivin gene sequence and its encoded amino acid sequence and used to generate survivin antibodies with high binding affinity. Also, identification of binding epitopes on survivin can be used in the design and construction of preferred antibodies. For example, a DNA encoding a preferred epitope on survivin may be recombinantly expressed and used to select an antibody which binds selectively to that epitope. The selected antibodies then are exposed to the sample under conditions sufficient to allow specific binding of the antibody to the specific binding epitope on survivin and the amount of complex formed then detected. Specific antibody methodologies are well understood and described in the literature. A more detailed description of their preparation can be found, for example, in Practical Immunology, Butt, W. R., ed., Marcel Dekker, New York, 1984.

The present invention also contemplates the detection of survivin antibodies. Survivin is a cancer specific marker. Thus, detection of survivin antibodies in biological fluids of a patient may enable the diagnosis of cancer.

Survivin Binding Partners

Other molecules that bind survivin can also be used to detect the presence of survivin in biological fluids. Examples of survivin binding partners, other than survivin antibodies, include but are not limited to p34$^{cdc2}$-cyclin Bl kinase and caspase-9.

Nucleic Acids

Nucleic acids including naturally occurring nucleic acids, oligonucleotides, antisense oligonucleotides, and synthetic oligonucleotides that hybridize to the nucleic acid encoding survivin, are useful as agents to detect the presence of survivin in the biological fluids of cancer patients, preferably in the urine of bladder cancer patients. Ambrosini et al. (Nat Med, 1997, 3: 917-921) disclose cloning of the survivin gene. Nucleic acids and oligonucleotides that are useful agents for the present invention include but are not limited to those corresponding to the survivin gene isolated by Ambrosini et al (Nat Med, 1997, 3:917-921). The present invention contemplates the use of nucleic acid sequences corresponding to the coding sequence of survivin and to the complementary sequence thereof, as well as sequences complementary to the survivin transcript sequences occurring further upstream or downstream from the coding sequence (e.g., sequences contained in, or extending into, the 5' and 3' untranslated regions) for use as agents for detecting the expression of survivin in biological fluids of cancer patients, preferably in the urine of bladder cancer patients.

The preferred oligonucleotides for detecting the presence of survivin in biological fluids are those that are complementary to at least part of the cDNA sequence encoding survivin. These complementary sequences are also known in the art as "antisense" sequences. These oligonucleotides may be oligoribonucleotides or oligodeoxyribonucleotides. In addition, oligonucleotides may be natural oligomers composed of the biologically significant nucleotides, i.e., A (adenine), dA (deoxyadenine), G (guanine), dG (deoxyguanine), C (cytosine), dC (deoxycytosine), T (thymine) and U (uracil), or modified oligonucleotide species, substituting, for example, a methyl group or a sulfur atom for a phosphate oxygen in the inter-nucleotide phosphodiester linkage. Additionally, these nucleotides themselves, and/or the ribose moieties may be modified.

The oligonucleotides may be synthesized chemically, using any of the known chemical oligonucleotide synthesis methods well described in the art. For example, the oligonucleotides are prepared by using any of the commercially available, automated nucleic acid synthesizers. Alternatively, the oligonucleotides may be created by standard recombinant DNA techniques, for example, inducing transcription of the noncoding strand. The DNA sequence encoding survivin may be inverted in a recombinant DNA system, e.g., inserted in reverse orientation downstream of a suitable promoter, such that the noncoding strand now is transcribed.

Although any length oligonucleotide may be utilized to hybridize to a nucleic acid encoding survivin, oligonucleotides typically within the range of 8-100 nucleotides are preferred. Most preferable oligonucleotides for use in detecting survivin in urine samples are those within the range of 15-50 nucleotides.

The oligonucleotide selected for hybridizing to the survivin nucleic acid, whether synthesized chemically or by recombinant DNA technology, is then isolated and purified using standard techniques and then preferably labeled (e.g., with $^{35}S$ or $^{32}P$) using standard labeling protocols.

The present invention also contemplates the use of oligonucleotide pairs in polymerize chain reactions (PCR) to detect the expression of survivin in biological fluids. The oligonucleotide pairs consist of a survivin primer and a reverse survivin primer. The preferred oligonucleotide pairs are SEQ ID NO: 1 and SEQ ID NO: 2. More preferably, the oligonucleotide pairs are SEQ ID NO: 3 and SEQ ID NO: 4.

3. Methods of Detection

Protein Binding Assays

As will be appreciated by those skilled in the art, any means for specifically identifying and quantifying a survivin protein in the biological fluid of a cancer patient is contemplated. The currently preferred means for detecting survivin protein in a sample is by means of a binding protein capable of interacting specifically with a marker protein. Preferably, labeled antibodies, binding portions thereof, or other survivin binding partners may be used. The antibodies may be monoclonal or polyclonal in origin, or may be biosynthetically produced. The survivin binding partners may also be naturally occurring molecules or synthetically produced. The amount of complexed survivin protein, e.g., the amount of survivin protein associated with the binding protein, is determined using standard protein detection methodologies described in the art. A detailed review of immunological assay design, theory and protocols can be found in numerous texts in the art, including Practical Immunology, Butt, W. R., ed., Marcel Dekker, New York, 1984.

A variety of assays are available for detecting proteins with labeled antibodies. In a one-step assay, the survivin molecule, if it is present, is immobilized and incubated with a labeled antibody. The labeled antibody binds to the immobilized target molecule. After washing to remove unbound molecules, the sample is assayed for the presence of the label.

In a two-step assay, immobilized survivin molecule is incubated with an unlabeled antibody. The survivin-unlabeled antibody complex, if present, is then bound to a second, labeled antibody that is specific for the unlabeled antibody. The sample is washed and assayed for the presence of the label.

The choice of marker used to label the antibodies will vary depending upon the application. However, the choice of the marker is readily determinable to one skilled in the art. These labeled antibodies may be used in immunoassays as well as in histological applications to detect the presence of tumors. The labeled antibodies may be polyclonal or monoclonal. In a preferred embodiment, the antibodies are polyclonal rabbit antibodies.

The antibodies may be labeled with a radioactive atom, an enzyme, a chromophoric or fluorescent moiety, or a colorimetric tag. The choice of tagging label also will depend on the detection limitations desired. Enzyme assays (ELISAs) typically allow detection of a colored product formed by interaction of the enzyme-tagged complex with an enzyme substrate. Some examples of radioactive atoms include $^{32}P$, $^{125}I$, $^{3}H$, and $^{14}P$. Some examples of enzymes include horseradish peroxidase, alkaline phosphatase, beta-galactosidase, and glucose-6-phosphate dehydrogenase. Some examples of chromophoric moieties include fluorescein and rhodamine. The antibodies may be conjugated to these labels by methods known in the art. For example, enzymes and chromophoric molecules may be conjugated to the antibodies by means of coupling agents, such as dialdehydes, carbodiimides, dimaleimides, and the like. Alternatively, conjugation may occur through a ligand-receptor pair. Some suitable ligand-receptor pairs include, for example, biotin-avidin or -streptavidin, and antibody-antigen.

The most sensitive label known to date is a chemiluminescent tag in which interaction of the tag with a reactant results in the production of light. Useful labels include chemiluminescent molecules such as acridium esters or chemiluminescent enzymes where the reactant is an enzyme substrate. When, for example, acridium esters are reacted with an alkaline peroxide solution, an intense flash of light is emitted, allowing the limit of detection to be increased 100 to 10,000 times over those provided by other labels. In addition, the reaction is rapid. A detailed review of chemiluminescence and immunoassays can be found in Weeks et al. (Methods in Enzymology, 1983, 133: 366-387), Kawaguichi et al. (Stabilized Phenyl Acridinium Esters For Chemiluminescent Immunoassay—Bioluminescence and Chemiluminescence, Proceedings of 9th International Symposium 1996, Edited by Hastings, Kricka and Stanley, John Wiley & Sons, 1997, pp. 480-484), and U.S. Pat. No. 5,468,646. Other considerations for fluid assays include the use of microtiter wells or column immunoassays. Column assays may be particularly advantageous where rapidly reacting labels, such as chemiluminescent labels, are used. The tagged complex can be eluted to a post-column detector which also contains the reactant or enzyme substrate, allowing the subsequent product formed to be detected immediately.

In one aspect, the present invention contemplates the use of a sandwich technique for detecting survivin proteins in serum and other biological fluids. As described in PCT Publication WO93/09437, published May 13, 1993, the technique requires two antibodies capable of binding the protein of interest: e.g., one immobilized onto a solid support, and one free in solution, but labeled with some easily detectable chemical compound. Examples of chemical labels that may be used for the second antibody include but are not limited to radioisotopes, fluorescent compounds, and enzymes or other molecules which generate colored or electrochemically active products when exposed to a reactant or enzyme substrate. When samples containing the survivin protein are placed in this system, the survivin protein binds to both the immobilized antibody and the labeled antibody. The result is a "sandwich" immune complex on the support's surface. The complexed protein is detected by washing away nonbound sample components and excess labeled antibody, and measuring the amount of labeled antibody complexed to protein on the support's surface. The sandwich immunoassay is highly specific and very sensitive, provided that labels with good limits of detection are used.

The present invention also contemplates screening numerous samples of biological fluids at the same time. This can be performed using the conventional 96-well microtiter format which is widely used and easily automatable. There are also several commercially available spectrometers ("plate readers") for calorimetrically analyzing 96-well plates.

Preferably, the presence of survivin in a sample of bodily fluid is detected by radioimmunoassays or enzyme-linked immunoassays, competitive binding enzyme-linked immunoassays, dot blot, Western blot, chromatography, preferably high performance liquid chromatography (HPLC), or other assays known in the art.

Dot blotting is routinely practiced by the skilled artisan to detect a desired protein using an antibody as a probe (Promega Protocols and Applications Guide, Second Edition, 1991, Page 263, Promega Corporation). Samples are applied to a membrane using a dot blot apparatus. A labeled probe is incubated with the membrane, and the presence of the protein is detected.

Western blot analysis is well known to the skilled artisan (Sambrook et al., Molecular Cloning, A Laboratory Manual, 1989, Vol. 3, Chapter 18, Cold Spring Harbor Laboratory). In Western blot, the sample is separated by SDS-PAGE. The gel is transferred to a membrane. The membrane is incubated with labeled antibody for detection of the desired protein.

The assays described above involve steps such as but not limited to, immunoblotting, immunodiffusion, immunoelectrophoresis, or immunoprecipitation.

Preferably, the survivin is detected by dot blotting or by Western blotting. More preferably, survivin is detected in the biological fluid of cancer patients by dot blotting using the Bio-Dot method and the Bio-Dot SF module.

Nucleic Acid Detection

The presence of survivin in a sample of biological fluid of a patient may also be determined by nucleic acid hybridization, such as but not limited to Northern blot analysis, dot blotting, Southern blot analysis, fluorescence in situ hybridization (FISH), and PCR. Chromatography, preferably HPLC, and other known assays may also be used to determine messenger RNA levels of survivin in a sample.

The survivin DNA conceivably may be found in the biological fluids inside a survivin-positive cancer cell that is being shed or released in the fluid under investigation.

In one aspect, the present invention contemplates the use of nucleic acids as agents for detecting survivin in biological fluids of patients, wherein the nucleic acids are labeled. The nucleic agents may be labeled with a radioactive label, a fluorescent label, an enzyme, a chemiluminescent tag, a calorimetric tag or other labels or tags that are discussed above or that are known in the art.

In another aspect, the present invention contemplates the use of Northern blot analysis to detect the presence of survivin mRNA in a sample of bodily fluid. The first step of the analysis involves separating a sample containing survivin nucleic acid by gel electrophoresis. The dispersed nucleic acids are then transferred to a nitrocellulose filter or another filter. Subsequently, the labeled oligonucleotide is exposed to the filter under suitable hybridizing conditions, e.g. 50% formamide, 5×SSPE, 2×Denhardt's solution, 0.1% SDS at 42° C., as described in Molecular Cloning: A Laboratory Manual, Maniatis et al. (1982, CSH Laboratory). Other useful procedures known in the art include solution hybridization, dot and slot RNA hybridization, and probe based microarrays. Measuring the radioactivity of hybridized fragments, using standard procedures known in the art quantitates the amount of survivin nucleic acid present in the biological fluid of a patient.

Dot blotting involves applying samples containing the nucleic acid of interest to a membrane. The nucleic acid can be denatured before or after application to the membrane. The membrane is incubated with a labeled probe. Dot blot procedures are well known to the skilled artisan and are described more fully in U.S. Pat. Nos. 4,582,789 and 4,617,261, the disclosures of which are incorporated herein by reference.

Polymerase chain reaction (PCR) is a process for amplifying one or more specific nucleic acid sequences present in a nucleic acid sample using primers and agents for polymerization and then detecting the amplified sequence. The extension product of one primer when hybridized to the other becomes a template for the production of the desired specific nucleic acid sequence, and vice versa, and the process is repeated as often as is necessary to produce the desired amount of the sequence. The skilled artisan to detect the presence of desired sequence (U.S. Pat. No. 4,683,195) routinely uses polymerase chain reaction.

A specific example of PCR that is routinely performed by the skilled artisan to detect desired sequences is reverse transcript PCR (RT-PCR; Saiki et al., Science, 1985, 230:1350; Scharf et al., Science, 1986, 233:1076). RT-PCR involves isolating total RNA from biological fluid, denaturing the RNA in the presence of primers that recognize the desired nucleic acid sequence, using the primers to generate a cDNA copy of the RNA by reverse transcription, amplifying the cDNA by PCR using specific primers, and detecting the amplified cDNA by electrophoresis or other methods known to the skilled artisan.

In a preferred embodiment, the methods of detecting survivin nucleic acid in biological fluids of cancer patients, preferably urine of bladder cancer patients, include Northern blot analysis, dot blotting, Southern blot analysis, FISH, and PCR. More preferably, the method of detection is RT-PCR using the following two sets of primers: SEQ ID NO: 1 and 2 and SEQ ID NO: 3 and 4.

4. Kits for Diagnosing Cancer

In one aspect, the present invention includes kits comprising the required elements for diagnosing cancer. Preferably, the kits comprise a container for collecting biological fluid from a patient and an agent for detecting the presence of survivin or its encoding nucleic acid in the fluid. The components of the kits can be packaged either in aqueous medium or in lyophilized form.

Kits for diagnosing or monitoring cancer containing one or more agents that detect the survivin protein, such as but not limited to survivin antibodies, fragments thereof, or survivin binding partners can be prepared. The agent(s) can be packaged with a container for collecting the biological fluid from a patient. When the antibodies or binding partner are used in the kits in the form of conjugates in which a label is attached, such as a radioactive metal ion or a moiety, the components of such conjugates can be supplied either in fully conjugated form, in the form of intermediates or as separate moieties to be conjugated by the user of the kit.

Kits containing one or more agents that detect survivin nucleic acid, such as but not limited to the full length survivin nucleic acid, survivin oligonucleotides, and pairs of survivin primers can also be prepared. The agent(s) can be packaged with a container for collecting biological fluid from a patient. The nucleic acid can be in the labeled form or to be labeled form.

Other components of the kit may include but are not limited to, means for collecting biological fluid, means for labeling the agent, membranes for immobilizing the survivin or survivin nucleic acid in the biological fluid, means for applying the biological fluid to the membrane, means for binding the agent to survivin in the biological fluid of a patient, a second antibody, a means for isolating total RNA from a biological fluid of a patient, means for performing gel electrophoresis, means for generating cDNA from isolated total RNA, means for performing hybridization assays, and means for performing PCR, etc.

5. Uses for Assays and Kits of the Present Invention

The assays or methods and kits of the present invention are useful for diagnosis, prognosis, and monitoring cancer in a patient. In one aspect of the invention, the presence of survivin in the biological fluid of a patient indicates that the patient has cancer. The cancer could be a new onset cancer or a recurrent cancer. As used herein, the term "recurrent cancer" means that the cancer has come back (recurred) after it has been treated. As used herein the term "new onset cancer" refers to newly developed cancer.

Survivin may be detected in biological fluids from any of the cancers where survivin is expressed and secreted, released, or found in a bodily fluid. Survivin is expressed in cancers of the lung, colon, pancreas, breast, prostate (Ambrosini et al., Nat. Med., 1997, 3:917-21), bladder (Swana et al., N. Engl. J. Med., 1999, 341: 452-53), and in non-Hodgkin's lymphoma. Expression of survivin in neuroblastoma, breast, lung bladder and colorectal cancers correlated with unfavorable disease and abbreviated survival (Adida et al., Lancet, 1998, 351: 882-83; Islam et al., Oncogene, 2000, 19: 617-23; Tanaka et al., Clin. Cancer Res., 2000, 6: 127-34; Monzo et al., J. Clin. Oncol., 1999, 17: 2100-04; Kawasaki et al., Cancer Res., 1998, 58: 5071-74; Swana et al., N. Engl. J. Med., 1999, 341: 452-53).

Survivin may be released by exfoliated cancer cells into the extracellular environment during tumor progression. Accordingly, any biological fluid from a patient can be assayed for the presence of survivin. Preferably, human bodily fluids such as prostatic fluid, seminal fluid, whole blood, serum, urine, breast biopsy fluid, gastrointestinal fluid, and vaginal fluid can be taken from a patient and screened for the presence of survivin.

In a preferred embodiment, the methods and kits of the present invention are used to diagnose genitourinary tract cancer including bladder cancer, prostate cancer, and renal cancer by detecting survivin in the biological fluids of patients. More preferably, the methods and kits of the present invention are used to diagnose bladder cancer by detecting the presence of survivin in the urine samples of patients. The presence of survivin in the urine samples of a patient indicates that the patient has bladder cancer.

In another aspect, the methods and kits of the present invention may be used to quantitate the amount of survivin in the biological fluid of a patient. The amount of survivin in the biological fluid of a patient may be useful for grading the cancer. A high level of survivin in the biological fluid of a patient may indicate that the cancer is of a high grade. Alternatively, the methods and kits of the present invention may be used to determine the stage of the cancer in a patient. A cancer of the CIS stage has a higher level of survivin than the cancer of the non-invasive papillary carcinoma stage.

As used herein, the term "papillary carcinoma" refers to a malignant neoplasm characterized by the formation of numerous, irregular, fingerlike projections of fibrous stroma that is covered with a surface layer of neoplastic epithelial cells.

As used herein, the term "carcinoma in situ (CIS)" is synonymous with intraepithelial carcinoma. The term when used to refer to bladder cancer means a flat tumor in the bladder lining (the transitional cells).

Further, the amount of survivin quantitated from the biological fluid of a patient may be used to monitor the progression of the cancer in the patient and to determine the prognosis of a cancer patient. For example, the amount of survivin measured over a period of time provides information as to how fast the cancer is growing.

Urine survivin can be used as a quick and inexpensive method for monitoring patients. The urine survivin test can be integrated in a battery of urine markers to improve the sensitivity and specificity of early detection of recurrences.

It is contemplated that after patients are tested positive for survivin in their biological fluids, they will be further tested using more invasive and expensive approaches, such as cystoscopy.

In light of the foregoing general discussion, the specific examples presented below are illustrative only and are not intended to limit the scope of the invention. Other generic and specific configurations will be apparent to those persons skilled in the art.

EXAMPLES

Materials and Methods

Urine Specimens: One hundred fifty eight urine specimens were collected at the urology clinics at Yale-New Haven Hospital and at the Veterans Administration, New England Health Care Systems, West Haven, Conn. Division. Random clean-catch or straight catheter urine samples were obtained from individuals who were categorized into 5 different groups. Group 1, normal healthy volunteers of mean age of 47.6±20.8 years taking no medications (n=17). Group 2, patients of mean age of 60.0±18.1 years with diagnosis of non-neoplastic urinary tract disease or hematuria (n=30). Group 3, patients of mean age of 71.5±9.9 years with diagnosis of genitourinary cancer, excluding bladder cancer (n=30). Group 4, patients of mean age of 69.7±8.7 years with diagnosis of new onset or recurrent bladder cancer (n=46). Group 5, patients of mean age of 76.1±8.9 years who were undergoing treatment or had already received treatment for bladder cancer and had a negative cytoscopic evaluation on the day of urine collection (n=35). Treatment measures in group 5 included intravesical bacillus Calmette-Guerin (BCG), thiotepa, transurethral resection, partial cystectomy and radiation. Group 4 included patients who after urine collection underwent similar treatment measures and/or salvage cystectomy or radical cystectomy.

Statistical Analysis: The relationship between urine survivin and patients' diagnosis was analyzed by a Chi square test. Non-parametric statistical analysis was used to compare the weighted urine survivin score with the grading classification system performed at the Yale-New Haven Hospital.

Example 1

Urine Detection of Survivin Using the Bio-Dot SF Module

Urine specimens were filtered onto a nitrocellulose membrane using a microfiltration apparatus in a module providing a 48-well slot format. The blot was analyzed for the presence of survivin using a polyclonal antibody. The protocol is as follows: urine was collected and stored at −80° C. until analysis. On the day of analysis, urine samples were centrifuged at 20,000×g for 20 min. Meanwhile, the Bio-Dot Microfiltration Apparatus was assembled with a 0.2 μm nitrocellulose membrane (Bio-Rad Laboratories, Hercules, Calif.) and moistened in 20 mM Tris-buffered saline (pH 7.5). Then, the urine supernatant (300 μl) along with increasing concentrations of E. coli-expressed recombinant survivin (Li et al., Nature, 1998, 396: 580-84) as a standard (0.001-1.0 μg/ml) in 300 μl of TBS were filtered onto the membrane. After filtration, the membrane was dried, blocked in 5% Blotto and 0.01% sodium azide in PBS, pH 7.4, for 12 h at 4° C. After washing in PBS-Tween 20 (0.25%), the membrane was incubated with 2 μg/ml of a rabbit antibody to survivin (Grossman et al., J. Invest. Dermatol., 1999, 113:1076-81.) for 3 h at 22° C., washed in PBS-Tween, and incubated with a 1:1000 dilution of horseradish peroxidase-conjugated donkey anti-rabbit IgG (Amersham Biotech, Piscataway N.J.) for 1 h at 22° C. After washes in PBS×2 for 10 min, PBS-Tween×2 for 5 min, and PBS×2 for 5 min, binding of the primary antibody was detected by enhanced chemiluminescence (Amersham) and autoradiography. Bands were quantitated by densitometry and a weighted survivin score was calculated on the basis of the antibody reactivity with increasing concentrations of recombinant survivin as follows: 0=not detectable; 1=0.001-0.25 µg/ml; 2=0.25-1 µg/ml; and 3=>1 µg/ml. Each urine specimen was analyzed at least twice on two different occasions and comparable results were obtained.

Example 2

Western Blotting

Urine specimens (100 ml) were centrifuged at 1,200×g for 10 min at 22° C., and the cell pellet was washed twice in TBS and solubilized in 0.5% Triton X-100 in the presence of protease inhibitors for 30 min at 4° C. Samples were separated by SDS gel electrophoresis, transferred to nylon membranes (Millipore, Corp.), and further incubated with 1 µg/ml of an antibody to survivin (Grossman et al., J. Invest. Dermatol., 1999, 113:1076-81) followed by horseradish peroxidase (HRP)-conjugated goat anti-rabbit IgG and chemiluminescence.

Example 3

RT-PCR

Fifty milliliters of clean catch urine was obtained from 15 patients with new or recurrent urothelial cancer, 2 patients with treated bladder cancer, 1 patient with prostate cancer, 1 patient with non-neoplastic urinary tract disease and 1 healthy volunteer. Total RNA was isolated from urine pellets using the Trizol reagent (Life Technologies, Inc., Gaithersburg, Md., USA). Single strand cDNA was synthesized by random priming of 1-5 µg total RNA using 1 µl of Superscript reverse transcriptase (Gibco BRL, Life Technologies, Inc., Gaithersburg, Md., USA) for 1 h at 43° C. After heating at 70° C. for 15 min, a first amplification reaction was carried out with survivin primers 5'-CTGCCTGGCAGCCCTTTCT-CAA-3' (forward; SEQ ID NO: 1) and 5'AATAAACCCTG-GAAGTGGTGCA-3' (reverse; SEQ ID NO: 2) with denaturation at 94° C. for 15 sec, annealing at 53° C. for 15 sec and extension at 72° C. for 1 min for 20 cycles, followed by incubation at 72° C. for 5 min. A 463-base pair (bp) fragment of the survivin cDNA was subjected to a second round of amplification with nested survivin primers 5'-CCGCATCTC-TACATTCAAGAAC-3' (forward; SEQ ID NO: 3) and 5'-CT-TGGCTCTTTCTCTGTCC-3' (reverse; SEQ ID NO: 4), with denaturation at 94° C. for 30 sec, annealing at 60° C. for 30 sec, and extension at 72° C. for 45 sec for 30 cycles, followed by incubation at 72° C. for 5 min. The amplified survivin cDNA of 279 bp was separated on a 2.0% agarose gel and visualized by ethidium bromide staining. Control reactions were amplified using β-actin-specific primers 5'-AGCGG-GAAATCGTGCGTG-3' (forward; SEQ ID NO: 5) and 5'-CAGGGTACATGGTGGTGCC-3' (reverse; SEQ ID NO: 6) with generation of a 309-bp fragment.

Results

Figure 1:
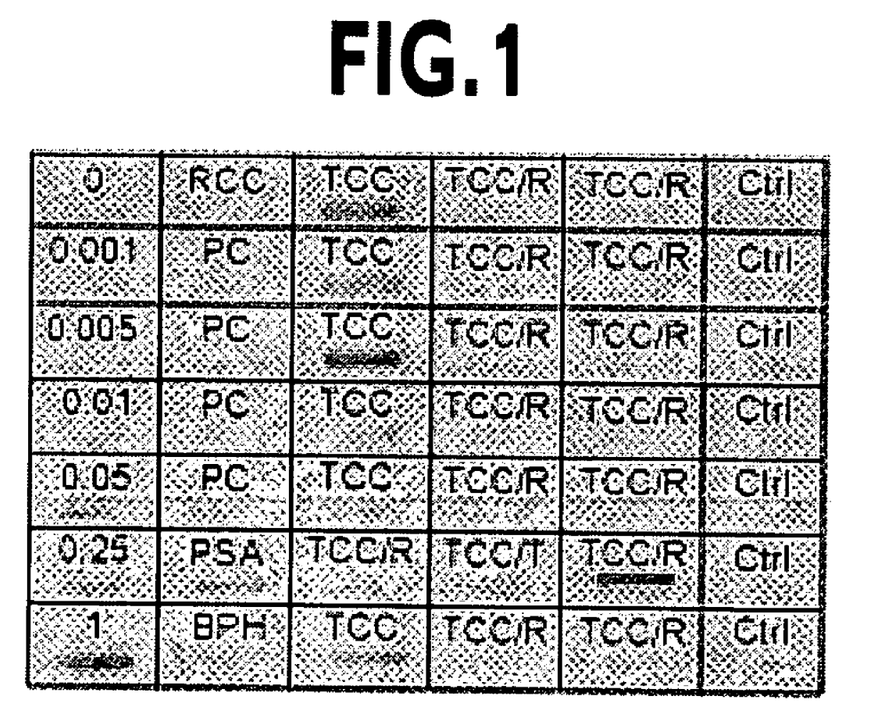
FIG. 1 shows urine detection of survivin using the Bio-Dot SF module. Increasing concentrations of recombinant survivin in μg/ml (left column), or urine specimens from the indicated patient groups were applied to a slot-blot apparatus. The membrane was incubated with an antibody to survivin followed by HRP-conjugated goat anti-rabbit IgG. Bands were visualized by chemiluminescence and quantitated by densitometry. TCC, bladder cancer (Group 4); TCC/R, remission (Group 5); TCC/T, under treatment (Group 5); RCC, renal cell carcinoma, PC, prostate cancer (Group 3); PSA, patient with rising PSA without diagnosis of prostate cancer (Group 2); BPH, benign prostate hyperplasia (Group 2); Ctrl, healthy volunteers (Group 1).

A representative experiment of detection of urine survivin using the Bio-Dot test is shown in FIG. 1. Determination of urine survivin with the Bio-Dot method was carried out in 138 out of the 158 specimens collected for this study (Table 1). Twenty additional urine samples were analyzed for survivin expression by RT-PCR to independently evaluate the specificity of the Bio-Dot method. Survivin was not detected in urine of normal volunteers (0/16), or patients with benign prostate hyperplasia (0/6), interstitial cystitis (0/2), renal calculi (0/3), urinary tract infection (0/6), or other non-neoplastic urinary tract disease (0/6) (Table 1). Urine survivin was detected in 3 out of 5 patients with cryptogenic hematuria (weighted survivin score, 2), who presented with a history of retention and dysuria post transurethral prostate resection, and revealed a trabeculated, irregularly thickened bladder, by cystoscopy. One patient with increased PSA levels but without diagnosis of prostate cancer was positive for urine survivin (Table 1). This patient also revealed a trabeculated, thickened bladder, by cystoscopy. Survivin was not detected in urine specimens of patients with prostate (0/19), renal (0/8), vaginal (0/1), or cervical (0/1) cancer (Table 1). In contrast, urine survivin was detected in all patients (31/31) with new onset or recurrent bladder cancer (Table 1). Histopathologic grading (grades I through IV) of the 31 patients in group 4 analyzed for urine survivin by Bio-Dot SF included 13 patients with grade II, seven patients with grade III, and five patients with grade IV tumors. Carcinoma in situ (CIS) was found in association with the papillary and invasive carcinomas of 5 patients and in association with high grade urothelial cancer of the ureter in one patient.

TABLE 1

Survivin Detection in 138 Urine Specimens by the Bio-Dot SF module.

| Urine specimens | (n) | Survivin-negative | Survivin-positive |
|---|---|---|---|
| Group 1 (control healthy volunteers) | 16 | 16 | 0 |
| Group 2 (Non-neoplastic urinary tract diseases) | 29 | | |
| Hematuria | 5 | 2 | 3 |
| UTI | 6 | 6 | 0 |
| BPH | 6 | 6 | 0 |
| Rising PSA | 1 | 0 | 1 |
| Interstitial cystitis | 2 | 2 | 0 |
| Renal calculi | 3 | 3 | 0 |
| Other† | 6 | 6 | 0 |
| Group 3 (Genito-urinary cancers except bladder) | 29 | | |
| Prostate | 19 | 19 | 0 |
| Renal | 8 | 8 | 0 |
| Vaginal | 1 | 1 | 0 |
| Cervical | 1 | 1 | 0 |
| Group 4 (new or recurrent bladder cancer) | 31§ | 0 | 31 |
| Group 5 (treated bladder cancer¶) | 33 | 30 | 3‡ |

UTI, urinary tract infection;
BPH, benign prostate hyperplasia;
PSA, prostate specific antigen.
†Includes patients with papillary necrosis (n = 1), prostatitis (n = 2), vesicouretral reflux (n = 1), and renal transplant with rising creatinine (n = 2).
§Includes one patient with urothelial cancer of the ureter.
¶Normal cystoscopy.
‡Two of these patients were treated with transurethral resection of the bladder tumor, and one with fulguration. One of these patients had urine cytology positive for bladder cancer.

Thirty of 33 patients in group 5 analyzed by Bio-Dot SF had no detectable urine survivin (Table 1). Five of these 30 patients were receiving BCG and had completed 3-5 treatments, the other 25 were status post-treatment with negative cystoscopy. Three patients in group 5 with initial diagnosis of GII non-invasive bladder cancer tested positive for urine survivin after undergoing negative cystoscopic examination. One of the 3 patients had urine cytology positive for bladder cancer. Two of the 3 patients were treated with transurethral resection of the bladder tumor and one was treated with fulguration.

When normalized for a weighted survivin score, patients with CIS had considerably higher survivin score (2.5 . . . 0.5, n=6) than patients with grade II bladder cancer (1.3 . . . 0.6, n=13). The correlation between weighted survivin score and histopathology or grading of the various bladder cancer cases is shown in Tables 2 and 3, respectively.

TABLE 2

Correlation Between Weighted Urine Survivin Score and Bladder Cancer Histopathology.

| Histopathology | Cases tested | Average survivin score |
|---|---|---|
| ND | 3 | 1.7 ± 1.2 |
| Non-invasive papillary carcinoma | 4 | 1 ± 0 |
| No detrusor muscle invasion | 12 | 1.6 ± 0.8 |
| Muscle invasion | 6 | 1.7 ± 0.8 |
| CIS | 6 | 2.5 ± 0.5† |

TABLE 3

Correlation Between Weighted Urine Survivin Score and Bladder Cancer Grading.

| Grade | Cases tested | Average survivin score |
|---|---|---|
| Grade II | 13 | 1.3 ± 0.6 |
| Grade III | 7 | 1.5 ± 0.8 |
| Grade IV | 5 | 2 ± 1 |
| Grade IV | 1 | 3* |

The weighted survivin score was calculated using a standard curve with increasing concentrations of recombiant survivin as follows:
0, not detectable;
1, 0.001–0.25 µg/ml;
2, 0.25–1 µg/ml; and
3, >1 µg/ml.
*One of the six patients with associated CIS had urothelial cancer of the ureter (Grade IV; surviven score, 3).
Histopathological analysis was carried out using the Broader's cytologic grading system for the classification of papillary transitional cell tumors, grades I–IV.
ND, not determined.
CIS, carcinoma in situ.
†Significantly greater than either Grade II or non-invasive papillary carcinoma (p < 0.02).

Figure 2:
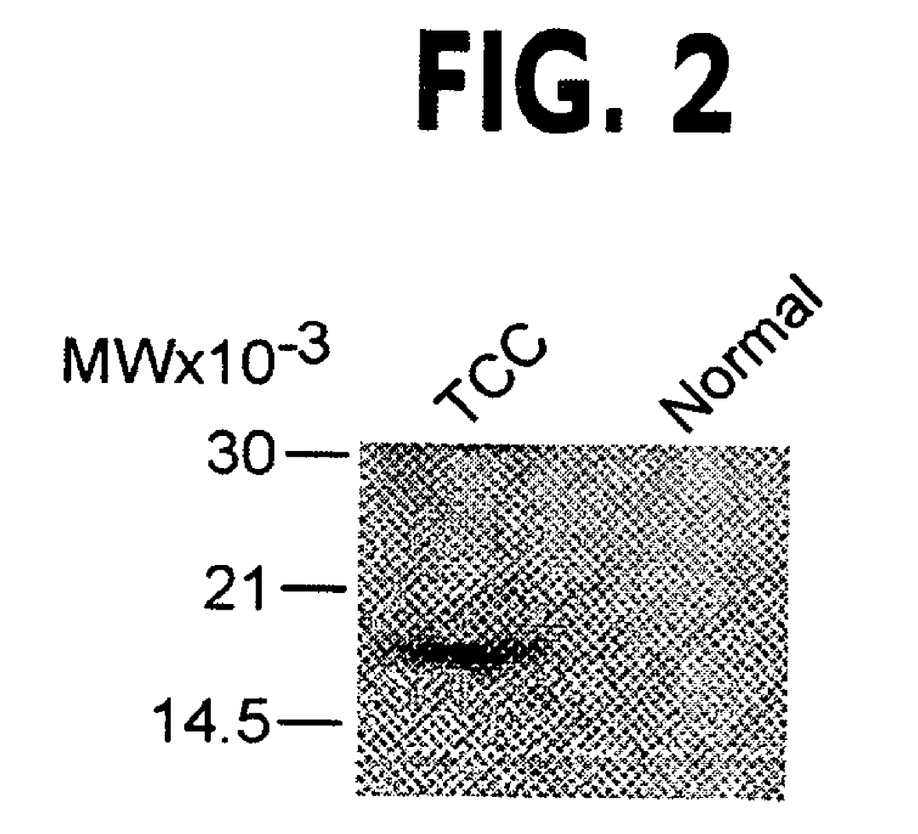
FIG. 2 shows Western blotting of urine survivin. Urine cell pellets from a normal healthy volunteer (Normal) and a Group 4 patient with bladder cancer (TCC) were electrophoresed, transferred to nylon membranes and immunoblotted with an antibody to survivin followed by chemiluminescence. Relative molecular weight markers are indicated on the left.

By Western blotting, a single survivin band of 16.5 kDa was detected in the urine cell pellet from a patient with bladder cancer but not in that from a healthy volunteer (FIG. 2).

Figure 3:
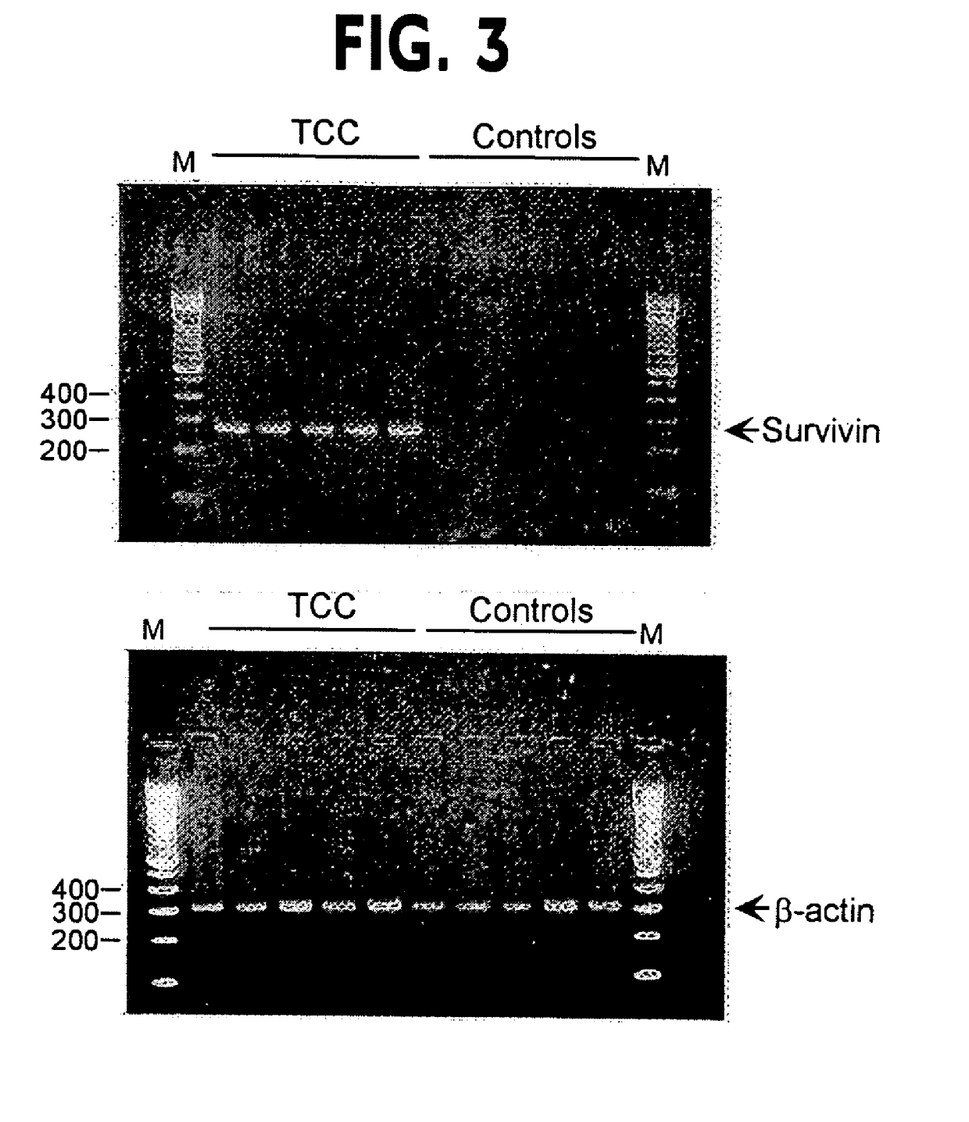
FIG. 3 shows RT-PCR amplification of survivin mRNA in urine. Total RNA was extracted from urine cell pellets and reverse-transcribed by random priming. Amplification reactions were carried out with survivin-specific nested primers (279 bp) or β-actin-specific primers (309 bp). Molecular weight markers in bp are indicated (M). TCC, analysis of 5 representative patients with new or recurrent bladder cancer (Group 4).
Figure 4:
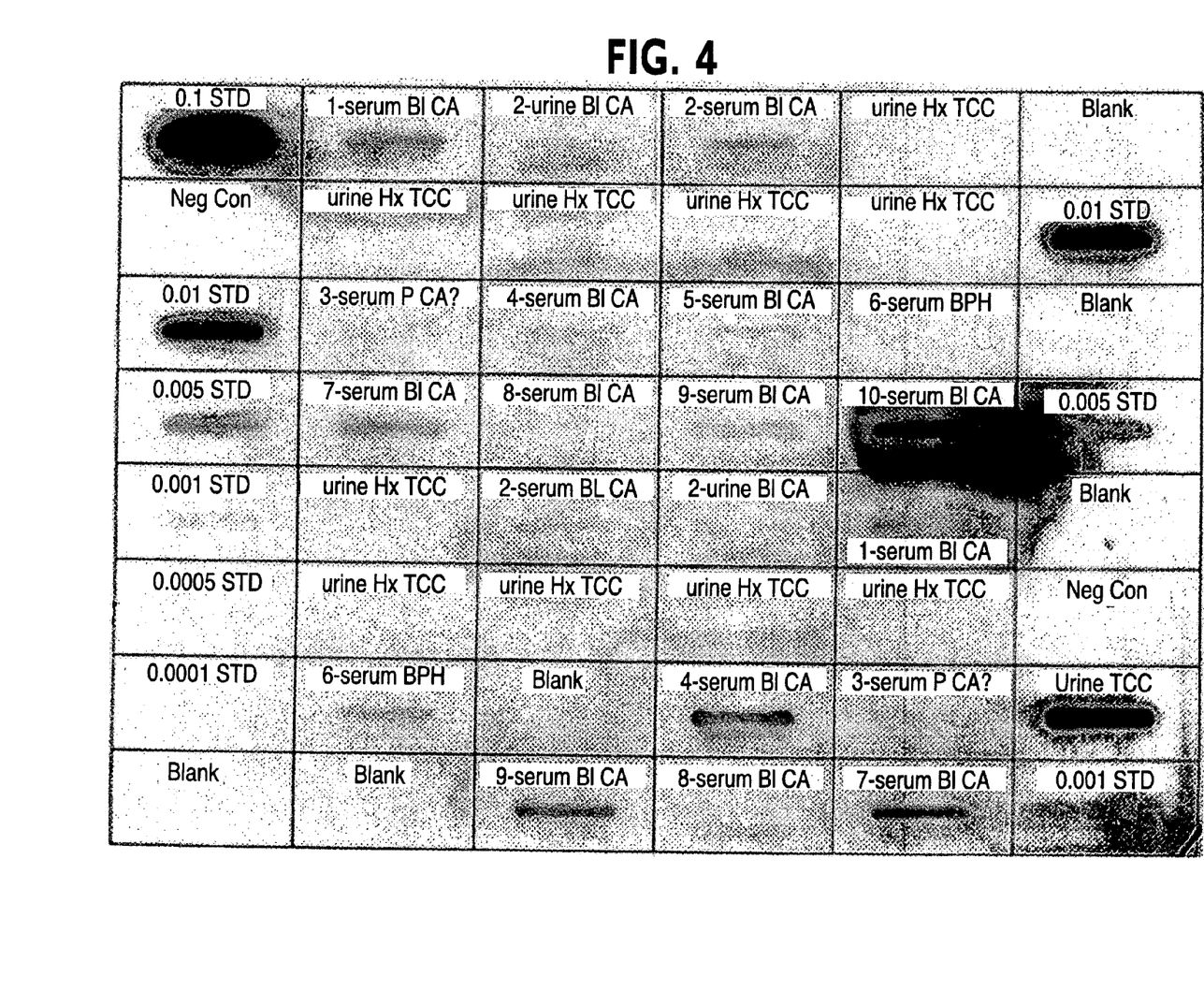

To independently evaluate the results obtained with the Bio-Dot method, 15 additional patients with new or recurrent bladder cancer were analyzed for urine survivin by RT-PCR. A 279 bp survivin cDNA was amplified from urine cell pellets of all the 15 new patients with bladder cancer (15/15) (FIG. 3 and data not shown). In contrast, urine cell pellets from 5 additional individuals, one with urinary tract infection, two with treated bladder cancer and negative cystoscopy, one with prostate cancer, and one from a normal volunteer, had no survivin cDNA (FIG. 3). In control experiments, a 309 bp β-actin cDNA fragment was indistinguishably amplified from urine of controls and patients with bladder cancer (FIG. 3). Histopathologic cases of bladder cancer analyzed by RT-PCR included five patients with grade II tumors, one patient with grade III, six patients with grade IV and 3 patients with CIS. These experiments suggest that exfoliated cancer cells passively release survivin in the extracellular milieu, i.e. urine, during tumor progression.

In the patient series examined here, the sensitivity of the urine survivin test for new or recurrent bladder cancer was 100%, and its specificity for other neoplastic and non-neoplastic genito-urinary diseases was 95% (p<0.02). Because of its high specificity, the urine survivin test may be useful to complement cytology and/or other diagnostics markers (Ramakumar et al., J. Urol. 1999, 161:388-94; Lokeshwar et al., J. Urol., 2000, 163:348-56) to better monitor bladder cancer patients and identify early recurrences or de novo neoplasms. Other potential advantages of the urine survivin test include its simplicity, suitability as a point-of-service procedure, and its cost-effectiveness, using one-step detection with a single antibody to survivin that has now become commercially available.

Example 4

Detection of Survivin in Blood Serum of Patients

Blood was collected from bladder and prostate cancer patients. The blood serum was isolated and tested for the presence of survivin by the dot blot method described in Example 1. Survivin was detected in the blood serum of bladder and prostate cancer patients. Increasing concentrations of recombinant survivin in µg/ml (left and right column), urine or serum samples were applied to a slot-blot apparatus. The membrane was incubated with an antibody to survivin followed by HRP-conjugated goat anti rabbit IgG. Bands were visualized by chemiluminescence.

The detection of survivin in blood serum of cancer patients indicates that survivin is useful as a marker for detecting other cancers. Testing the serum for the presence of survivin is useful for screening and for detection of recurrences and relapses of cancer.

It should be understood that the foregoing discussion and examples merely present a detailed description of certain preferred embodiments. It therefore should be apparent to those of ordinary skill in the art that various modifications and equivalents can be made without departing from the spirit and scope of the invention. All journal articles, other references, patents, and patent applications that are identified in this patent application are incorporated by reference in their entirety.

The invention claimed is:

1. A method of diagnosing cancer in a patient comprising performing an assay on a sample of biological fluid from a patient wherein the assay comprises a single detection step that consists of detecting only the presence or absence of survivin in the sample, wherein the presence of survivin indicates that the patient has cancer.

2. The method of claim 1, wherein the cancer is any cancer invading the genitourinary tract.

3. The method for claim 2, wherein the genitourinary tract cancer is bladder or prostate cancer.

4. The method of claim 3, wherein the bladder or prostate cancer is graded as a carcinoma in situ ("CIS").

5. The method of claim 3, wherein the bladder or prostate cancer is any grade or any stage.

6. The method of claim 1, wherein survivin is detected using an agent selected from the group consisting of antibodies that bind survivin, survivin binding partners, and nucleic acids that hybridize to a nucleic acid encoding survivin.

7. The method of claim 6, wherein the agent is tagged with a label.

8. The method of claim 7, wherein the label is a radioactive label, a fluorescent label, an enzyme, or a chemiluminescent tag.

9. The method of claim 1, wherein survivin is detected by an immunoassay.

10. The method of claim 9, wherein the immunoassay is an enzyme linked immunosorbent assay or radioimmunoassay.

11. The method of claim 9, wherein the immunoassay comprises immunoblotting, immunodiffusion, immunoelectrophoresis, or immunoprecipitation.

12. The method of claim 1, wherein survivin is detected by dot blotting.

13. The method of claim 12, wherein dot blotting comprises using a Bio-Dot SF module.

14. The method of claim 1, wherein survivin is detected by nucleic acid hybridization.

15. The method of claim 14, wherein the nucleic acid hybridization is RT-PCR or Northern blot analysis.

16. A kit for the diagnosis, prognosis, or monitoring of cancer, comprising a container for collecting a biological fluid from a patient and a means for detecting survivin, wherein the means for detecting survivin consists of a single detection agent that detects only the presence of survivin in the biological fluid.

17. The kit of claim 16, wherein the agent is selected from the group consisting of antibodies that bind survivin, survivin binding partners, and nucleic acids that hybridize to the nucleic acid encoding survivin.

18. The kit of claim 17, wherein the agent is tagged with a label.

19. The kit of claim 17, wherein the label is a radioactive label, a fluorescent label, an enzyme, or a chemiluminescent tag.

20. The kit of claim 16, wherein the agent is packaged in an aqueous medium or in lyophilized form.

21. The kit of claim 16, further comprising a component for analyzing the presence of survivin.

22. The kit of claim 16, wherein the cancer is bladder or prostate cancer.

23. A method of determining the grade of a cancer in a patient comprising a single detection step that consists of detecting only the presence of survivin in a sample of biological fluid from a patient and quantitating and normalizing only the amount of survivin in the sample and comparing the amount of survivin in the sample with the amount of survivin in control samples to determine the grade of the cancer in the patient.

24. A method of determining the stage of a cancer in a patient comprising a single detection step that consists of detecting only the presence of survivin in a sample of biological fluid from a patient and quantitating and normalizing only the amount of survivin in the sample and comparing the amount of survivin in the sample with the amount of survivin in control samples to determine the stage of the cancer in the patient.

25. A method of monitoring cancer in a patient comprising a single detection step that consists of detecting only the presence of survivin in a sample of biological fluid from a patient and quantitating and normalizing only the amount of survivin in the sample.

26. The method of claim 1, wherein the cancer is any cancer that expresses survivin.

27. The method of claim 1, wherein the cancer is selected from the group consisting of neuroblastoma, breast cancer, lung cancer, bladder cancer, colorectal cancer, pancreatic cancer, genitourinary tract cancer, prostate cancer, renal cancer, and bladder cancer.

28. The method of claim 1, wherein the cancer is new onset cancer or recurrent cancer.

29. The method of claim 1, wherein the method of claim 1 has a sensitivity of 100% and wherein the cancer is bladder cancer.

30. The method of claim 1, wherein the method of claim 1 has a specificity of 95% and wherein the sample is from a patient with other neoplastic or non-neoplastic genito-urinary diseases than new or recurrent bladder cancer.

31. The method of claim 1, wherein the biological fluid comprises nucleic acid or protein.

32. The method of claim 1, wherein the biological fluid comprises cellular debris.

33. The method of claim 31, wherein the cellular debris comprises protein or nucleic acid.

34. The method of claim 31, wherein the cellular debris comprises exfoliated cells or transitional cells.

35. The method of claim 1, wherein the method further comprises obtaining a pellet from the biological fluid prior to the detection step and the detection step consists of detecting only the presence or absence of survivin in the pellet.

36. The method of claim 35, wherein the pellet is obtained by centrifugation, filtration, chromatography, or combinations thereof.

37. The method of claim 35, wherein the pellet comprises cellular debris.

38. The method of claim 37, wherein the cellular debris comprises exfoliated cells or transitional cells.

39. The method of claim 35, wherein the method further comprises solubilizing the pellet.

40. The method of claim 1, wherein the method further comprises separating out the supernatant from the biological fluid to obtain a pellet prior to the detection step.

41. The method of claim 40, wherein the detection step consists of detecting only the presence or absence of survivin in the pellet.

42. The method of claim 40, wherein the detection step consists of detecting only the presence or absence of survivin in the supernatant.

43. The method of claim 1, wherein the biological fluid is selected from the group consisting of whole urine, whole blood, bodily fluid, prostatic fluid, breast biopsy fluid, gastrointestinal fluid, and vaginal fluid.

44. The method of claim 16, wherein the biological fluid is selected from the group consisting of whole urine, whole blood, whole bodily fluid, prostatic fluid, breast biopsy fluid, gastrointestinal fluid, and vaginal fluid.

45. The method of claim 23, wherein the biological fluid is selected from the group consisting of whole urine, whole blood, bodily fluid, prostatic fluid, breast biopsy fluid, gastrointestinal fluid, and vaginal fluid.

46. The method of claim 24, wherein the biological fluid is selected from the group consisting of whole urine, whole blood, bodily fluid, prostatic fluid, breast biopsy fluid, gastrointestinal fluid, and vaginal fluid.

47. The method of claim 25, wherein the biological fluid is selected from the group consisting of whole urine, whole blood, bodily fluid, prostatic fluid, breast biopsy fluid, gastrointestinal fluid, and vaginal fluid.

* * * * *

SEQUENCE LISTING

<160> NUMBER OF SEQ ID NOS: 6

<210> SEQ ID NO 1
<211> LENGTH: 22
<212> TYPE: DNA
<213> ORGANISM: Artificial Sequence
<220> FEATURE:
<223> OTHER INFORMATION: Description of Artificial Sequence: Forward PCR primer

```
<400> SEQUENCE: 1
ctgcctggca gcctttctc aa                                              22

<210> SEQ ID NO 2
<211> LENGTH: 22
<212> TYPE: DNA
<213> ORGANISM: Artificial Sequence
<220> FEATURE:
<223> OTHER INFORMATION: Description of Artificial Sequence:  Reverse
      PCR primer

<400> SEQUENCE: 2
aataaaccct ggaagtggtg ca                                             22

<210> SEQ ID NO 3
<211> LENGTH: 22
<212> TYPE: DNA
<213> ORGANISM: Artificial Sequence
<220> FEATURE:
<223> OTHER INFORMATION: Description of Artificial Sequence:  Forward
      PCR primer

<400> SEQUENCE: 3
ccgcatctct acattcaaga ac                                             22

<210> SEQ ID NO 4
<211> LENGTH: 19
<212> TYPE: DNA
<213> ORGANISM: Artificial Sequence
<220> FEATURE:
<223> OTHER INFORMATION: Description of Artificial Sequence:  Reverse
      PCR primer

<400> SEQUENCE: 4
cttggctctt tctctgtcc                                                 19

<210> SEQ ID NO 5
<211> LENGTH: 18
<212> TYPE: DNA
<213> ORGANISM: Artificial Sequence
<220> FEATURE:
<223> OTHER INFORMATION: Description of Artificial Sequence:  Forward
      PCR primer

<400> SEQUENCE: 5
agcgggaaat cgtgcgtg                                                  18

<210> SEQ ID NO 6
<211> LENGTH: 19
<212> TYPE: DNA
<213> ORGANISM: Artificial Sequence
<220> FEATURE:
<223> OTHER INFORMATION: Description of Artificial Sequence:  Reverse
      PCR primer

<400> SEQUENCE: 6
cagggtacat ggtggtgcc                                                 19
```